US008399829B2

(12) United States Patent
Yang et al.

(10) Patent No.: US 8,399,829 B2
(45) Date of Patent: Mar. 19, 2013

(54) VITAMIN B2 DETECTION BY MASS SPECTROMETRY

(75) Inventors: Changming Yang, Aliso Viejo, CA (US); Sum Chan, San Clemente, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 194 days.

(21) Appl. No.: 12/365,080

(22) Filed: Feb. 3, 2009

(65) Prior Publication Data

US 2010/0155592 A1    Jun. 24, 2010

Related U.S. Application Data

(60) Provisional application No. 61/138,909, filed on Dec. 18, 2008.

(51) Int. Cl.
*B01D 59/44* (2006.01)
*G01N 33/82* (2006.01)

(52) U.S. Cl. .................... 250/288; 250/282; 436/98

(58) Field of Classification Search ............... 250/282, 250/288; 436/96, 98
See application file for complete search history.

(56) References Cited

U.S. PATENT DOCUMENTS

| | | | |
|---|---|---|---|
| 5,772,874 A | 6/1998 | Quinn et al. | |
| 5,795,469 A | 8/1998 | Quinn et al. | |
| 5,919,368 A | 7/1999 | Quinn et al. | |
| 5,968,367 A | 10/1999 | Quinn et al. | |
| 6,107,623 A | 8/2000 | Bateman et al. | |
| 6,124,137 A | 9/2000 | Hutchens et al. | |
| 6,204,500 B1 | 3/2001 | Whitehouse et al. | |
| 6,268,144 B1 | 7/2001 | Köster | |
| 7,972,867 B2 * | 7/2011 | Clarke et al. | 436/173 |
| 2008/0311671 A1 * | 12/2008 | Jiang et al. | 436/96 |
| 2009/0155766 A1 * | 6/2009 | Goldman et al. | 435/4 |

OTHER PUBLICATIONS

Midttun, et al, "Multianalyte Quantification of Vitamin B6 and B2 Species in the Nanomolar Range in Human Plasma by Liquid-Chromatography-Tandem Mass Spectroscopy", Clinical Chemistry 51:7, p. 1206-1216, 2006.*
Zimmer et. al., "Comparison of Turbulent-Flow Chromatography With Automated Solid-Phase Extraction in 96-Well Plates and Liquid-Liquid Extraction Used as Plasma Sample Preparation Techniques for Liquid Chromatography-Tandem Mass Spectrometry", Journal of Chromatography A, 854 (1999), p. 23-25.*
Chen et. al., "LC/UC/MS-MRM for the Simultaneous Determination of Water-Soluble Vitamins in Multi-Vitamin Dietary Supplements", Anal. Bioanal. Chem., 387:2441-2448, 2007.*
Midttun, et. al. "Multianalyte Quantification of Vitamin B6 and B2 Species in the Nanomolar Range in Human Plasma by Liquid Chromatography-Tandem Mass Spectroscopy", Clinical Chemistry 51:7 p. 1206-1216, 2006.*
Zimmer et. al. "Comparison of Turbulent-Flow Liquid Chromatography With Automated Solid-Phase Extraction in 96-Well Plates and Liquid-Liquid Extraction Used as a Plasma Sample Preparation Techniques for Liquid Chromatography Tandem Mass Spectrometry", Journal of Chromatography A, 854 (1999), p. 23-25.*
Chen, et. al. "LC/UV/MS-MRM for the Simultaneous Determination of Water-Soluable Vitamins in Multi-Vitamin Dietary Supplements", Anal. Bioanal. Chem, 387, 2441-2448, 2007.*

(Continued)

*Primary Examiner* — Robert Kim
*Assistant Examiner* — David E Smith
(74) *Attorney, Agent, or Firm* — Foley & Lardner LLP

(57) ABSTRACT

Methods are described for measuring the amount of a vitamin B2 in a sample. More specifically, mass spectrometric methods are described for detecting and quantifying vitamin B2 in a sample utilizing on-line extraction methods coupled with tandem mass spectrometric techniques.

2 Claims, 5 Drawing Sheets

OTHER PUBLICATIONS

Ekinci and Kadakal, "Determination of Seven Water-Soluble Vitamins in Tarhana, a Traditional Turkish Cereal Food, by High-Performance Liquid Chromatography", Acta Chromatographica, No. 15, 2005.*

Midttun et. al, "Multianalyte Quantification of Vitamin B6 and B2 Species in the Nanomolar Range in Human Plasma by Liquid Chromatography-Tandem Mass Spectrometry", Clinical Chemistry 51:7, p. 1206-1216, 2006.*

Zimmer et. al. "Comparison of Turbulent-Flow Chromatograophy With Automated Solid-Phase Extraction in 96-Well Plates and Liquid Liquid Extraction Used as Plasma Sample Preparation Techniques for Liquid Chromatography-Tandem Mass Spectrometry", Journal of Chromatography A, 854 (1999), p. 23-25.*

Chen, et. al. "LC/UV/MS-MRM for the Simulataneous Determination of Water-Soluble Vitamins in Multi-Vitamin Dietary Supplements", Anal. Bioanal. Chem, 387:2441-2448, 2007.*

Ekinci, "Determination of Seven Water-Soluble Vitamins in Tarhana, A Traditional Turkish Cereal Food, By High-Performance Liquid Chromatography", Acta Chromatographia, No. 15, 2005, p. 289-297.*

Anyakora, et. al. "HPLC Analysis of Nicotinamide, Pyridoxine, Riboflavin and Thiamin in Some Selected Food Products in Nigeria", African Journal of Pharmacy and Pharmacology vol. 2 (2) pp. 029-036, Apr. 2008.*

Midttun et al, "Multianalyte Quantification of Vitamin B6 and B2 Species in the Nanomolar Range in Human Plasma by Liquid-Chromatography-Tandem Mass Spectroscopy", Clinical Chemistry 51:7 p. 1206-1216, 2006.*

Chen et al, "LC/UV/MS-MRM for the Simultaneous Determination of Water-Soluble Vitamins in Multi-Vitamin Dietary Supplements", Anal. Bioanal. Chem, 387, 2441-2448, 2007.*

Ekinici and Kadakai, "Determination of Seven Water-Soluble Vitamins in Tarhana, a Traditional Turkish Cereal Food, by High-Performance Liquid Chromatography", Acta Chromatographica, No. 15, 2005.*

Aranda and Morlock, Simultaneous determination of riboflavin, pyridoxine, nicotinamide, caffeine and taurine in energy drinks by planar chromatography-multiple detection with confirmation by electrospray ionization mass spectrometry, *J. Chromatogr.A.*, 1131:253-60, (2006).

Bartolucci, et al., Liquid chromatography tandem mass spectrometric quantitation of sulfamethazine and its metabolites: direct analysis of swine urine by triple quadrupole and by ion trap mass spectrometry, *Rapid Commun. Mass Spectrom.*, 14:967-73 (2000).

Chen, P., LC/UV/MS-MRM for the simultaneous determination of water-soluble vitamins in multi-vitamin dietary supplements, *Anal Bioanal Chem*, 387:2441-8 (2007).

Gentili, et al., Simultaneous determination of water-soluble vitamins in selected food matrices by liquid chromatography/electrospray ionization tandem mass spectrometry, *Rapid Commun. Mass Spectrom.*, 22:2029-43 (2008).

Grant and Helleur, Simultaneous analysis of vitamins and caffeine in energy drinks by surfactant-mediated matrix-assisted laser desorption/ionization, *Anal Bioanal Chem*, 391:2811-2818 (2008).

Guo, et al., HPLC-MS Analysis of the Riboflavin Crude Product of Semisynthesis, *J. Chromatographic Science*, 44:552-6 (2006).

Leporati, A., et al., Application of a liquid chromatography tandem mass spectrometry method to the analysis of water-soluble vitamins in Italian pasta, *Analytica Chimica Acta*, 531:87-95 (2004).

Merchant and Weinberger, Recent advancements in surface-enhanced laser desorption/ionization-time of flight-mass spectrometry, *Electrophoresis*, 21: 1164-67 (2000).

Midttun, Ø., et al., Multianalyte Quantification of Vitamin $B_6$ and $B_2$ Species in the Nanomolar Range in Human Plasma by Liquid Chromatrography-Tandem Mass Spectrometry, *Clin. Chem.*, 51:1206-16 (2005).

Polson et al., Optimization of protein precipitation based upon effectiveness of protein removal and ionization effect in liquid chromatography-tandem mass spectrometry, *Journal of Chromatography B*, 785:263-275 (2003).

Robb et al., Atmospheric Pressure Photoionization: An Ionization Method for Liquid Chromatography-Mass Spectrometry, *Anal. Chem.*, 72(15): 3653-3659 (2000).

Wright et al., Proteinchip® surface enhanced laser desorption/ionization (SELDI) mass spectrometry: a novel protein biochip technology for detection of prostate cancer biomarkers in complex protein mixtures, *Prostate Cancer and Prostatic Diseases*, 2: 264-76 (1999).

Zimmer et al., Comparison of turbulent-flow chromatrography with automated solid-phase extraction in 96-well plates and liquid-liquid extraction used as plasma sample preparation techniques for liquid chromatography-tandem mass spectrometry, *J Chromatogr A*, 854: 23-35 (1999).

Zougagh and Rios, Supercritical fluid extraction as an on-line cleanup technique for determination of riboflavin vitamins in food samples by capillary electrophoresis with fluorimetric detection, *Electrophoresis*, 29:3213-9 (2008).

Steinar Hustad et al., "Quantification of Riboflavin, Flavin Mononucleotide, and Flavin Adenine Dinucleotide in Human Plasma by Capillary Electrophoresis and Laser-induced Fluorescence Detection", *Clinical Chemistry* 45:6, 862-868, 1999.

* cited by examiner

Channel 1 (Day 1)

Channel 1 (Day 2)

Channel 2 (Day 1)

Channel 2 (Day 2)

Channel 3 (Day 1)

Channel 3 (Day 2)

VITAMIN B2 DETECTION BY MASS SPECTROMETRY

CROSS REFERENCE TO RELATED APPLICATION

The present application claims priority to U.S. Provisional Patent Application Ser. No. 61/138,909 filed Dec. 18 2008, which is incorporated by reference in its entirety herein

FIELD OF THE INVENTION

The invention relates to the quantitative measurement of vitamin B2. In a particular aspect, the invention relates to methods for quantitative measurement of vitamin B2 by HPLC-tandem mass spectrometry.

BACKGROUND OF THE INVENTION

The following description of the background of the invention is provided simply as an aid in understanding the invention and is not admitted to describe or constitute prior art to the invention.

Vitamin B2 (also known as riboflavin) is one of eight water-soluble B vitamins. It is the central component of the cofactors flavin adenine dinucleotide (FAD) and flavin mononucleotide (FMN), and is therefore required by all flavoproteins. As such, vitamin B2 is required for a wide variety of cellular processes. Like the other B vitamins, it plays a key role in energy metabolism, and is required for the metabolism of fats, ketone bodies, carbohydrates, and proteins. Vitamin B2 is also required for the health of the mucus membranes in the digestive tract and helps with the absorption of iron and Vitamin B6.

Riboflavin is continuously excreted in the urine of healthy individuals, making deficiency relatively common when dietary intake is insufficient. However, a deficiency of riboflavin may also be due to secondary causes, i.e., the result of conditions that affect absorption in the intestine, the body's inability to use vitamin B2, or an increase in the excretion of vitamin B2 from the body.

In humans, signs and symptoms of riboflavin deficiency (ariboflavinosis) include cracked and red lips, inflammation of the lining of mouth and tongue, mouth ulcers, cracks at the corners of the mouth (angular cheilitis), and sore throat. A deficiency may also cause dry and scaling skin, fluid in the mucous membranes, and iron-deficiency anemia. The eyes may also become bloodshot, itchy, watery and sensitive to bright light.

Riboflavin deficiency is classically associated with the oral-ocular-genital syndrome. Angular cheilitis, photophobia, and scrotal dermatitis are the classic remembered signs.

Methods have been reported for extracting vitamin B from food/drink samples or dietary supplements. See, e.g., Leporati, A., et al., *Analytica Chimica Acta* 2004, 531 :87-95; Zougagh M, et al., *Electrophoresis* 2008, 29:3213-9; Chen, P., et al., *Anal Rioanal Chem* 2007, 387:2441-8; Aranda, et al., *J. Chromatogr. A* 2006, 1131:253-60; Gentili, et al., *Rapid Commun. Mass Spectrom.* 2008, 22:2029-43; and Grant, D., et al., *Anal Bioanal Chem* 2008, 391:2811-2818. Additionally, various mass spectrometric techniques for measuring vitamin B2 in a sample have been reported. See, e.g., Leporati, A., et al., *Analytica Chimica Acta* 2004, 531:87-95; Guo, et al., *J. Chromatographic Science* 2006, 44:552-6; Midttun, Ø., et al., *Clin. Chem.* 2005, 51:1206-16; Chen, P., et al., *Anal Bioanal Chem* 2007, 387:2441-8; and Grant, D., et al., *Anal Bioanal Chem* 2008,391:2811-2818.

SUMMARY OF THE INVENTION

The present invention provides methods for detecting the presence or amount of vitamin B2 in a sample by tandem mass spectrometry. Preferably, the methods of the invention include a solid phase extraction method coupled with high performance liquid chromatography.

In one aspect, methods are provided for determining the amount of vitamin B2 in a biological sample. In some embodiments, the methods include: (a) subjecting the sample, purified by solid phase extraction (SPE), to ionization under conditions suitable to produce one or more ions detectable by mass spectrometry; (b) determining the amount of one or more ions by tandem mass spectrometry; and (c) using the amount of the one or more ions to determine the amount of vitamin B2 in the sample. In some embodiments, SPE comprises turbulent flow liquid chromatography (TFLC). In some embodiments, SPE and tandem mass spectrometry are conducted with on-line processing. In some embodiments, the sample purified by SPE has been further purified by high performance liquid chromatography (HPLC) prior to ionization; preferably with on-line processing. In some embodiments, the one or more ions detected by tandem mass spectrometry are selected from the group consisting of ions with mass to charge ratio of 377.2±0.5 and 243.2±0.5. The features of the embodiments listed above may be combined without limitation for use in methods of the present invention.

In other embodiments, methods for determining the amount of vitamin B2 in a sample include: (a) subjecting the sample, purified by turbulent flow chromatography (TFLC) and high performance liquid chromatography (HPLC), to ionization under conditions suitable to produce one or more ions detectable by mass spectrometry; wherein one or more ions detectable by mass spectrometry comprise one or more ions from the group consisting of ions with a mass to charge ratio of 377.2±0.5 and 243.2±0.5; (b) determining the amount of one or more ions by tandem mass spectrometry; and (c) using the amount of the one or more ions to determine the amount of vitamin B2 in the sample. In some embodiments, the TFLC and HPLC are conducted as on-line processing of the sample prior to mass spectrometry. In some embodiments, the one or more ions detectable by mass spectrometry comprise a parent ion with a mass to charge ratio of 377.2±0.5 and a fragment ion with a mass to charge ratio of 243.2±0.5. The features of the embodiments listed above may be combined without limitation for use in methods of the present invention.

Methods of the present invention may involve the combination of liquid chromatogaphy with mass spectrometry. In preferred embodiments, the liquid chromatography is TFLC. One preferred embodiment utilizes TFLC in combination with one or more purification methods such as for example SPE (e.g., TFLC) and/or protein precipitation and filtration, to purify an analyte in a sample. In some embodiments, at least one purification step and mass spectrometric analysis is conducted in an on-line fashion. In another preferred embodiment, the mass spectrometry is tandem mass spectrometry (MS/MS).

In certain preferred embodiments of the methods disclosed herein, mass spectrometry is performed in positive ion mode. Alternatively, mass spectrometry is performed in negative ion mode. Various ionization sources, including for example atmospheric pressure chemical ionization (APCI) or electrospray ionization (ESI), may be used in embodiments of the present invention. In certain preferred embodiments, vitamin B2 is measured using ESI in positive ion mode.

In some preferred embodiments, vitamin B2 ions detectable in a mass spectrometer are selected from the group consisting of positive ions with a mass/charge ratio (m/z) of 377.20±0.50 and 243.20±0.50. In particularly preferred embodiments, a vitamin B2 precursor ion has m/z of 377.20±0.50, and a fragment ion has m/z of 243.20±0.50.

In preferred embodiments, a separately detectable internal standard is provided in the sample, the amount of which is also determined in the sample. In these embodiments, all or a portion of both the analyte of interest and the internal standard present in the sample is ionized to produce a plurality of ions detectable in a mass spectrometer, and one or more ions produced from each are detected by mass spectrometry. Preferably, the internal standard is $^{13}C, ^{15}N_2$-vitamin B2. In these embodiments, $^{13}C, ^{15}N_2$-vitamin B2 ions detectable in a mass spectrometer are selected from the group consisting of positive ions with a mass/charge ratio (m/z) of 380.20±0.50 and 243.20±0.50. In particularly preferred embodiments, a $^{13}C, ^{15}N,$-vitamin B2 precursor ion has m/z of 380.20±0.50, and a fragment ion has m/z of 243.20±0.50. In these embodiments, the presence or amount of ions generated from the analyte of interest may be related to the presence of amount of analyte of interest in the sample.

In other embodiments, the amount of the vitamin B2 ion or ions may be determined by comparison to one or more external reference standards. Exemplary external reference standards include blank plasma or serum spiked with vitamin B2 or $^{13}C, ^{15}N,$-vitamin B2.

In certain preferred embodiments, the limit of quantitation (LOQ) of vitamin B2 is within the range of 5 nmol/L to 25 nmol/L, inclusive; preferably within the range of 5 nmol/L to 20 nmol/L, inclusive; preferably within the range of 5 nmol/L to 15 nmol/L, inclusive; preferably within the range of 5 nmol/L to 10 nmol/L, inclusive; preferably about 5 nmol/L.

As used herein, unless otherwise stated, the singular forms "a," "an," and "the" include plural reference. Thus, for example, a reference to "a protein" includes a plurality of protein molecules.

As used herein, the term "purification" or "purifying" does not refer to removing all materials from the sample other than the analyte(s) of interest. Instead, purification refers to a procedure that enriches the amount of one or more analytes of interest relative to other components in the sample that may interfere with detection of the analyte of interest. Purification of the sample by various means may allow relative reduction of one or more interfering substances, e.g., one or more substances that may or may not interfere with the detection of selected parent or daughter ions by mass spectrometry. Relative reduction as this term is used does not require that any substance, present with the analyte of interest in the material to be purified, is entirely removed by purification.

As used herein, the term "sample" refers to any sample that may contain an analyte of interest. As used herein, the term "body fluid" means any fluid that can be isolated from the body of an individual. For example, "body fluid" may include blood, plasma, serum, bile, saliva, urine, tears, perspiration, and the like. In preferred embodiments, the sample comprises a body fluid sample; preferably plasma or serum.

As used herein, the term "solid phase extraction" or "SPE" refers to a process in which a chemical mixture is separated into components as a result of the affinity of components dissolved or suspended in a solution (i.e., mobile phase) for a solid through or around which the solution is passed (i.e., solid phase). In some instances, as the mobile phase passes through or around the solid phase, undesired components of the mobile phase may be retained by the solid phase resulting in a purification of the analyte in the mobile phase. In other instances, the analyte may be retained by the solid phase, allowing undesired components of the mobile phase to pass through or around the solid phase. In these instances, a second mobile phase is then used to elute the retained analyte off of the solid phase for further processing or analysis. SPE, including TFLC, may operate via a unitary or mixed mode mechanism. Mixed mode mechanisms utilize ion exchange and hydrophobic retention in the same column; for example, the solid phase of a mixed-mode SPE column may exhibit strong anion exchange and hydrophobic retention; or may exhibit column exhibit strong cation exchange and hydrophobic retention.

As used herein, the term "chromatography" refers to a process in which a chemical mixture carried by a liquid or gas is separated into components as a result of differential distribution of the chemical entities as they flow around or over a stationary liquid or solid phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of "liquid chromatography" include reverse phase liquid chromatography (RPLC), high performance liquid chromatography (HPLC), and turbulent flow liquid chromatography (TFLC) (sometimes known as high turbulence liquid chromatography (HTLC) or high throughput liquid chromatography).

As used herein, the term "high performance liquid chromatography" or "HPLC" (sometimes known as "high pressure liquid chromatography") refers to liquid chromatography in which the degree of separation is increased by forcing the mobile phase under pressure through a stationary phase, typically a densely packed column.

As used herein, the term "turbulent flow liquid chromatography" or "TFLC" (sometimes known as high turbulence liquid chromatography or high throughput liquid chromatography) refers to a form of chromatography that utilizes turbulent flow of the material being assayed through the column packing as the basis for performing the separation. TFLC has been applied in the preparation of samples containing two unnamed drugs prior to analysis by mass spectrometry. See, e.g., Zimmer et al., *J Chromatogr A* 854: 23-35 (1999); see also, U.S. Pat. No. 5,968,367, 5,919,368, 5,795,469, and 5,772,874, which further explain TFLC. Persons of ordinary skill in the art understand "turbulent flow". When fluid flows slowly and smoothly, the flow is called "laminar flow". For example, fluid moving through an HPLC column at low flow rates is laminar. In laminar flow the motion of the particles of fluid is orderly with particles moving generally in straight lines. At faster velocities, the inertia of the water overcomes fluid frictional forces and turbulent flow results. Fluid not in contact with the irregular boundary "outruns" that which is slowed by friction or deflected by an uneven surface. When a fluid is flowing turbulently, it flows in eddies and whirls (or vortices), with more "drag" than when the flow is laminar. Many references are available for assisting in determining when fluid flow is laminar or turbulent (e.g., *Turbulent Flow Analysis: Measurement and Prediction*, P. S. Bernard & J. M. Wallace, John Wiley & Sons, Inc., (2000); *An Introduction to Turbulent Flow*, Jean Mathieu & Julian Scott, Cambridge University Press (2001)).

As used herein, the term "gas chromatography" or "GC" refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase.

As used herein, the term "large particle column" or "extraction column" refers to a chromatography column containing an average particle diameter greater than about 50 μm. As used in this context, the term "about" means ±10%.

As used herein, the term "analytical column" refers to a chromatography column having sufficient chromatographic plates to effect a separation of materials in a sample that elute from the column sufficient to allow a determination of the presence or amount of an analyte. Such columns are often distinguished from "extraction columns", which have the general purpose of separating or extracting retained material from non-retained materials in order to obtain a purified sample for further analysis. As used in this context, the term "about" means ±10%. In a preferred embodiment the analytical column contains particles of about 5 μm in diameter.

As used herein, the terms "on-line" and "inline", for example as used in "on-line automated fashion" or "on-line extraction" refers to a procedure performed without the need for operator intervention. In contrast, the term "off-line" as used herein refers to a procedure requiring manual intervention of an operator. Thus, if samples are subjected to precipitation, and the supernatants are then manually loaded into an autosampler, the precipitation and loading steps are off-line from the subsequent steps. In various embodiments of the methods, one or more steps may be performed in an on-line automated fashion.

As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrometric instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., *Prostate Cancer and Prostatic Diseases* 1999, 2: 264-76; and Merchant and Weinberger, *Electrophoresis* 2000, 21: 1164-67.

As used herein, the term "operating in negative ion mode" refers to those mass spectrometry methods where negative ions are generated and detected. The term "operating in positive ion mode" as used herein, refers to those mass spectrometry methods where positive ions are generated and detected.

As used herein, the term "ionization" or "ionizing" refers to the process of generating an analyte ion having a net electrical charge equal to one or more electron units. Negative ions are those having a net negative charge of one or more electron units, while positive ions are those having a net positive charge of one or more electron units.

As used herein, the term "electron ionization" or "EI" refers to methods in which an analyte of interest in a gaseous or vapor phase interacts with a flow of electrons. Impact of the electrons with the analyte produces analyte ions, which may then be subjected to a mass spectrometry technique.

As used herein, the term "chemical ionization" or "CI" refers to methods in which a reagent gas (e.g. ammonia) is subjected to electron impact, and analyte ions are formed by the interaction of reagent gas ions and analyte molecules.

As used herein, the term "fast atom bombardment" or "FAB" refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

As used herein, the term "matrix-assisted laser desorption ionization" or "MALDI" refers to methods in which a non-volatile sample is exposed to laser irradiation, which desorbs and ionizes analytes in the sample by various ionization pathways, including photo-ionization, protonation, deprotonation, and cluster decay. For MALDI, the sample is mixed with an energy-absorbing matrix, which facilitates desorption of analyte molecules.

As used herein, the term "surface enhanced laser desorption ionization" or "SELDI" refers to another method in which a non-volatile sample is exposed to laser irradiation, which desorbs and ionizes analytes in the sample by various ionization pathways, including photo-ionization, protonation, deprotonation., and cluster decay. For SELDI, the sample is typically bound to a surface that preferentially retains one or more analytes of interest. As in MALDI., this process may also employ an energy-absorbing material to facilitate ionization.

As used herein, the term "electrospray ionization" or; "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber. As the droplets get smaller the electrical surface charge density increases until such time that the natural repulsion between like charges causes ions as well as neutral molecules to be released.

As used herein, the term "atmospheric pressure chemical ionization" or "APCI," refers to mass spectrometry methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "atmospheric pressure photoionization" or "APPI" as used herein refers to the form of mass spectrometry where the mechanism for the photoionization of molecule M is photon absorption and electron ejection to form the molecular ion M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+. See. e.g., Robb et al, *Anal. Chem.* 2000, 72(15): 3653-3659.

As used herein, the term "inductively coupled plasma" or "ICP" refers to methods in which a sample interacts with a partially ionized gas at a sufficiently high temperature such that most elements are atomized and ionized.

As used herein, the term "field desorption" refers to methods in which a non-volatile test sample is placed on an ionization surface, and an intense electric field is used to generate analyte ions.

As used herein, the term "desorption" refers to the removal of an analyte from a surface and/or the entry of an analyte into a gaseous phase. Laser desorption thermal desorption is a technique wherein a sample containing the analyte is thermally desorbed into the gas phase by a laser pulse. The laser hits the back of a specially made 96-well plate with a metal base. The laser pulse heats the base and the heat causes the sample to transfer into the gas phase. The gas phase sample is then drawn into the mass spectrometer.

As used herein, the term "selective ion monitoring" is a detection mode for a mass spectrometric instrument in which only ions within a relatively narrow mass range, typically about one mass unit, are detected.

As used herein, "multiple reaction mode," sometimes known as "selected reaction monitoring," is a detection mode for a mass spectrometric instrument in which a precursor ion and one or more fragment ions are selectively detected.

As used herein, the term "lower limit of quantification", "lower limit of quantitation" or "LLOQ" refers to the point where measurements become quantitatively meaningful. The analyte response at this LOQ is identifiable, discrete and reproducible with a relative standard deviation (RSD %) of less than 20% and an accuracy of 85% to 115%.

As used herein, the term "limit of detection" or "LOD" is the point at which the measured value is larger than the uncertainty associated with it. The LOD is the point at which a value is beyond the uncertainty associated with its measurement and is defined as three times the RSD of the mean at the zero concentration.

As used herein, an "amount" of an analyte in a body fluid sample refers generally to an absolute value reflecting the mass of the analyte detectable in volume of sample. However, an amount also contemplates a relative amount in comparison to another analyte amount. For example, an amount of an analyte in a sample can be an amount which is greater than a control or normal level of the analyte normally present in the sample.

The term "about" as used herein in reference to quantitative measurements not including the measurement of the mass of an ion, refers to the indicated value plus or minus 10%. Mass spectrometry instruments can vary slightly in determining the mass of a given analyte. The term "about" in the context of the mass of an ion or the mass/charge ratio of an ion refers to ±0.50 atomic mass unit.

The summary of the invention described above is non-limiting and other features and advantages of the invention will be apparent from the following detailed description of the invention, and from the claims.

DETAILED DESCRIPTION OF THE INVENTION

Figure 1A:
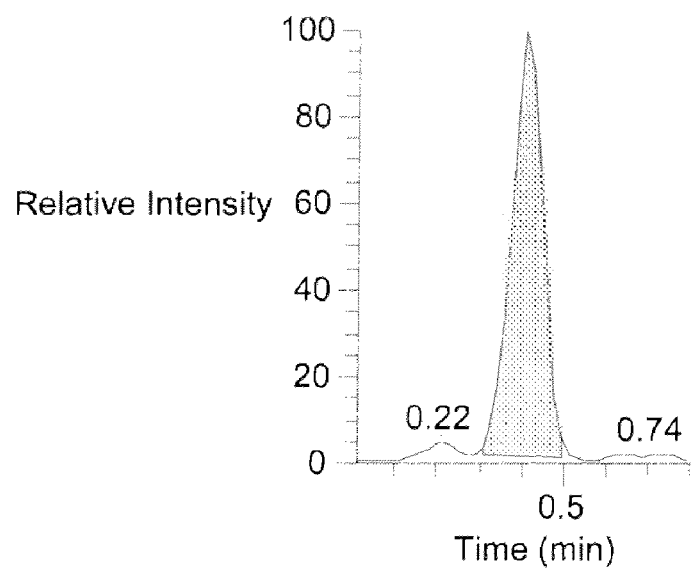
FIGS. 1A-B show exemplary chromatograms for vitamin B2 and $^{13}C$, $^{15}N_2$-vitamin B2 (internal standard), respectively. Details are discussed in Example 3.

Methods are described for measuring the amount of vitamin B2 in a sample. More specifically, mass spectrometric methods are described for detecting and quantifying vitamin B2 in a sample. The methods may utilize turbulent flow liquid chromatography (TFLC), to perform a purification of selected analytes, combined with methods of mass spectrometry (MS), thereby providing a high-throughput assay system for detecting and quantifying vitamin B2 in a sample. The preferred embodiments are particularly well suited for application in large clinical laboratories for automated vitamin B2 quantification assay.

Suitable test samples for use in methods of the present invention include any test sample that may contain the analyte of interest. In some preferred embodiments, a sample is a biological sample; that is, a sample obtained from any biological source, such as an animal, a cell culture, an organ culture, etc. In certain preferred embodiments, samples are obtained from a mammalian animal, such as a dog, cat, horse, etc. Particularly preferred mammalian animals are primates, most preferably male or female humans. Preferred samples comprise bodily fluids such as blood, plasma, serum, saliva, cerebrospinal fluid, or tissue samples; preferably plasma and serum; most preferably EDTA plasma. Such samples may be obtained, for example, from a patient; that is, a living person, male or female, presenting oneself in a clinical setting for diagnosis, prognosis, or treatment of a disease or condition.

The present invention also contemplates kits for a vitamin B2 quantitation assay. A kit for a vitamin B2 quantitation assay may include a kit comprising the compositions provided herein. For example, a kit may include packaging material and measured amounts of an isotopically labeled internal standard, in amounts sufficient for at least one assay. Typically, the kits will also include instructions recorded in a tangible form (e.g., contained on paper or an electronic medium) for using the packaged reagents for use in a vitamin B2 quantitation assay.

Calibration and QC pools for use in embodiments of the present invention are preferably prepared using a matrix similar to the intended sample matrix, provided that vitamin B2 is essentially absent. Commercially available EDTA plasma often contains a significant amount of Vitamin B2; thus in preferred embodiments, blank human serum (without vitamin B2, such as Biocell Laboratories, Inc., Cat. No. 1131-00) is used for calibration and QC pools.

Sample Preparation for Mass Spectrometric Analysis

Typically, frozen test samples (including controls) are thawed rapidly and kept protected from light exposure to minimize vitamin B2 degradation. Internal standard may be added to the test samples once they are thawed.

In preparation for mass spectrometric analysis, vitamin B2 may be enriched relative to one, or more other components in the sample (e.g. protein) by various methods known in the art, including for example, liquid chromatography, filtration, centrifgation, thin layer chromatography (TLC), electrophoresis including capillary electrophoresis, affinity separations including immunoaffinity separations, extraction methods including ethyl acetate or methanol extraction, and the use of chaotropic agents or any combination of the above or the like.

Protein precipitation is one method of preparing a test sample, especially a biological test sample, such as serum or plasma. Protein purification methods are well known in the art, for example, Polson et al., *Journal of Chromatography B* 2003, 785:263-275, describes protein precipitation techniques suitable for use in methods of the present invention. Protein precipitation may be used to remove most of the protein from the sample leaving vitamin B2 in the supernatant. The samples may be centrifuged to separate the liquid supernatant from the precipitated proteins; alternatively the samples may be filtered to remove precipitated proteins. The resultant supernatant or filtrate may then be applied directly to mass spectrometry analysis; or alternatively to liquid chromatography and subsequent mass spectrometry analysis. In certain embodiments, the use of protein precipitation such as for example, formic acid protein precipitation, may obviate the need for TFLC or other on-line extraction prior to mass spectrometry or HPLC and mass spectrometry.

Another method of sample purification that may be used prior to mass spectrometry is liquid chromatography (LC). Certain methods of liquid chromatography, including HPLC, rely on relatively slow, laminar flow technology. Traditional HPLC analysis relies on column packing in which laminar flow of the sample through the column is the basis for separation of the analyte of interest from the sample. The skilled artisan will understand that separation in such columns is a partition process and may select LC, including HPLC, instruments and columns that are suitable for use with vitamin B2. The chromatographic column typically includes a medium (i.e., a packing material) to facilitate separation of chemical moieties (i.e., fractionation). The medium max include minute particles. The particles typically include a bonded surface that interacts with the various chemical moieties to facilitate separation of the chemical moieties. One suitable bonded surface is a hydrophobic bonded surface such as an alkyl bonded or a cyano bonded surface. Alkyl bonded surfaces may include C-4, C-8, C-12, or C-18 bonded alkyl groups. In preferred embodiments, the column is a C-18 column. The chromatographic column includes an inlet port for receiving a sample and an outlet port for discharging an effluent that includes the fractionated sample. The sample may be supplied to the inlet port directly, or from a SPE column, such as an on-line TFLC column.

In one embodiment, the sample may be applied to the LC column at the inlet port? eluted with a solvent or solvent mixture, and discharged at the outlet port. Different solvent modes may be selected for eluting the analyte(s) of interest. For example, liquid chromatography may be performed using a gradient mode, an isocratic mode, or a polytyptic (i.e. mixed) mode. During chromatography, the separation of materials is effected by variables such as choice of eluent (also known as a "mobile phase"), elution mode, gradient conditions, temperature, etc.

In certain embodiments, an analyte may be purified by applying a sample to a column under conditions where the analyte of interest is reversibly retained by the column packing material, while one or more other materials are not retained. In these embodiments, a first mobile phase condition can be employed where the analyte of interest is retained by the column, and a second mobile phase condition can subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. Such procedures may enrich the amount of one or more analytes of interest relative to one or more other components of the sample.

In one preferred embodiment, HPLC is conducted with a polar embedded analytical column chromatographic system. In certain preferred embodiments, a polar embedded C-18 analytical column (e.g., an Atlantis T3 analytical column from Waters Corp. (5 μm particle size, 50×4.6 mm), or equivalent) is used. In certain preferred embodiments, HPLC and/or TFLC are performed using HPLC Grade acetonitrile, water, 0.1% aqueous formic acid, 0.1% formic acid in acetonitrile, and a solution of acetonitrile, water, 0.5% ammonium formate, and 0.1% formic acid as mobile phases.

By careful selection of valves and connector plumbing, two or more chromatography columns may be connected as needed such that material is passed from one to the next without the need for any manual steps. In preferred embodiments, the selection of valves and plumbing is controlled by a computer pre-programmed to perform the necessary steps. Most preferably, the chromatography system is also connected in such an on-line fashion to the detector system, e.g., an MS system. Thus, an operator may place a tray of samples in an autosampler, and the remaining operations are performed under computer control, resulting in purification and analysis of all samples selected.

In some embodiments, TFLC may be used for purification of vitamin B2 prior to mass spectrometry. In such embodiments, samples may be extracted using a TFLC column which captures the analyte, then eluted and chromatographed on a second TFLC column or on an analytical HPLC column. For example, sample extraction with a TFLC extraction cartridge may be accomplished with a large particle size (50 μm) packed column. Sample eluted off of this column may then be transferred to an HPLC analytical column for further purification prior to mass spectrometry. In preferred embodiments, a mixed mode material with both strong cation exchange and reversed phase binding capacity (e.g., a Cyclone MCX column from Cohesive Technologies, Inc. (60 μm particle size, 1.0×50 mm), or equivalent) is used. Because the steps involved in these chromatography procedures may be linked in an automated fashion, the requirement for operator involvement during the purification of the analyte can be minimized. This feature may result in savings of time and costs, and eliminate the opportunity for operator error.

Detection and Quantitation by Mass Spectrometry

In various embodiments, vitamin B2 present in a test sample may be ionized by any method known to the skilled artisan. Mass spectrometry is performed using a mass spectrometer, which includes an ion source for ionizing the fractionated sample and creating charged molecules for further analysis. For example ionization of the sample may be performed by electron ionization, chemical ionization, electrospray ionization (ESI), photon ionization, atmospheric pressure chemical ionization (APCI), photoionization, atmospheric pressure photoionization (APPI), fast atom bombardment (FAB), liquid secondary ionization (LSI), matrix assisted laser desorption ionization (MALDI), field ionization, field desorption, thermnospray/plasmaspray ionization, surface enhanced laser desorption ionization (SELDI), inductively coupled plasma (ICP) and particle beam ionization. The skilled artisan will understand that the choice of ionization method may be determined based on the analyte to be measured, type of sample, the type of detector, the choice of positive versus negative mode, etc.

Vitamin B2 may be ionized in positive or negative mode. In preferred embodiments, vitamin B2 is ionized by ESI in positive mode. In related preferred embodiments, vitamin B2 ions are in a gaseous state and the inert collision gas is argon or nitrogen; preferably argon.

In mass spectrometry techniques generally, after the sample has been ionized, the positively or negatively charged ions thereby created may be analyzed to determine a mass-to-charge ratio. Suitable analyzers for determining mass-to-charge ratios include quadrupole analyzers, ion traps analyzers, and time-of-flight analyzers. Exemplary ion trap methods are described in Bartolucci, et al., *Rapid Commun. Mass Spectrom.* 2000, 14:967-73.

The ions may be detected using several detection modes. For example, selected ions may be detected, i.e. using a selective ion monitoring mode (SIM), or alternatively, ions may be detected using a scanning mode, e.g., multiple reaction monitoring (MRM) or selected reaction monitoring (SRM). Preferably, the mass-to-charge ratio is determined using a quadrupole analyzer. For example, in a "quadrupole" or "quadrupole ion trap" instrument, ions in an oscillating radio frequency field experience a force proportional to the DC potential applied between electrodes, the amplitude of the RF signal, and the mass/charge ratio. The voltage and amplitude may be selected so that only ions having a particular mass/charge ratio travel the length of the quadrupole, while all other ions are deflected. Thus, quadrupole instruments may act as both a "mass filter" and as a "mass detector" for the ions injected into the instrument.

One may enhance the resolution of the MS technique by employing "tandem mass spectrometry," or "MS/MS". In this technique, a precursor ion (also called a parent ion) generated from a molecule of interest can be filtered in an MS instrument, and the precursor ion subsequently fragmented to yield one or more fragment ions (also called daughter ions or product ions) that are then analyzed in a second MS procedure. By careful selection of precursor ions, only ions produced by certain analytes are passed to the fragmentation chamber, where collisions with atoms of an inert gas produce the fragment ions. Because both the precursor and fragment ions are produced in a reproducible fashion under a given set of ionization/fragmentation conditions, the MS/MS technique may provide an extremely powerful analytical tool. For example, the combination of filtration/fragmentation may be used to eliminate interfering substances, and may be particularly useful in complex samples, such as biological samples.

The mass spectrometer typically provides the user with an ion scan; that is, the relative abundance of each ion with a particular mass/charge over a given range (e.g., 100 to 2000 amu). The results of an analyte assay, that is, a mass spectrum, may be related to the amount of the analyte in the original sample by numerous methods known in the art. For example, given that sampling and analysis parameters are carefully controlled, the relative abundance of a given ion may be compared to a table that converts that relative abundance to an absolute amount of the original molecule. Alternatively, external standards may be run with the samples, and a standard curve constructed based on ions generated from those standards. Using such a standard curve, the relative abundance of a given ion may be converted into an absolute amount of the original molecule. In certain preferred embodiments, an internal standard is used to generate a standard curve for calculating the quantity of vitamin B2. Methods of generating and using such standard curves are well known in the art and one of ordinary skill is capable of selecting an appropriate internal standard. For example, in preferred embodiments isotopically labeled vitamin B2 (e.g., $^{13}$C, $^{15}$N$_2$-vitamin B2) may be used as an internal standard. Numerous other methods for relating the amount of an ion to the amount of the original molecule will be well known to those of ordinary skill in the art.

As used herein, an "isotopic label" produces a mass shift in the labeled molecule relative to the unlabeled molecule when analyzed by mass spectrometric techniques. Examples of suitable labels include deuterium, $^{13}$C, and $^{15}$N. For example, $^{13}$C, 15N$_2$-vitamin B2 has a mass about three units higher than vitamin B2. The isotopic label can be incorporated at one or more positions in the molecule and one or more kinds of isotopic labels can be used on the same isotopically labeled molecule.

One or more steps of the methods may be performed using automated machines. In certain embodiments, one or more purification steps are performed on-line, and more preferably all of the purification and mass spectrometry steps may be performed in an on-line fashion.

In certain embodiments, such as MS/MS, where precursor ions are isolated for further fragmentation, collision activated dissociation (CAD) is often used to generate fragment ions for further detection. In CAD, precursor ions gain energy through collisions with an inert gas, and subsequently fragment by a process referred to as "unimolecular decomposition." Sufficient energy must be deposited in the precursor ion so that certain bonds within the ion can be broken due to increased vibrational energy.

In particularly preferred embodiments, vitamin B2 in a sample is detected and/or quantified using MS/MS as follows. The samples are subjected to liquid chromatography, preferably TFLC followed by HPLC; the flow of liquid solvent from a chromatographic column enters the heated nebulizer interface of an MS/MS analyzer; and the solvent/analyte mixture is converted to vapor in the heated charged tubing of the interface. During these processes, the analyte (i.e., vitamin B2) is analyzed. The ions, e.g. precursor ions, pass through the orifice of the instrument and enter the first quadrupole. Quadrupoles 1 and 3 (Q1 and Q3) are mass filters, allowing selection of ions (i.e., selection of "precursor" and "fragment" ions in Q1 and Q3, respectively) based on their mass to charge ratio (m/z). Quadrupole 2 (Q2) is the collision cell, where ions are fragmented. The first quadrupole of the mass spectrometer (Q1) selects for molecules with the mass to charge ratios of vitamin B2. Precursor ions with the correct mass/charge ratios are allowed to pass into the collision chamber (Q2), while unwanted ions with any other mass/charge ratio collide with the sides of the quadrupole and are eliminated. Precursor ions entering Q2 collide with neutral argon gas molecules and fragment. The fragment ions generated are passed into quadrupole 3 (Q3), where the fragment ions of vitamin B2 are selected while other ions are eliminated, The methods may involve MS/MS performed in either positive or negative ion mode; preferably positive ion mode. Using standard methods well known in the art, one of ordinary skill is capable of identifying one or more fragment ions of a particular precursor ion of vitamin B2 that may be used for selection in quadrupole 3 (Q3).

As ions collide with the detector they produce a pulse of electrons that are converted to a digital signal. The acquired data is relayed to a computer, which plots counts of the ions collected versus time. The resulting mass chromatograms are similar to chromatograms generated in traditional HPLC-MS methods. The areas under the peaks corresponding to particular ions, or the amplitude of such peaks, may be measured and correlated to the amount of the analyte of interest. In certain embodiments, the area under the curves, or amplitude of the peaks, for fragment ion(s) and/or precursor ions are measured to determine the amount of vitamin B2. As described above, the relative abundance of a given ion may be converted into an absolute amount of the original analyte using calibration standard curves based on peaks of one or more ions of an internal molecular standard.

The following Examples serve to illustrate the invention. These Examples are in no way intended to limit the scope of the methods. In particular, the following Examples demonstrate quantitation of vitamin B2 by mass spectrometry with the use of $^{13}C$, $^{15}N_2$-vitamin B2 as an internal standard. The use of $^{13}C$, $^{15}N$-vitamin B2 as an internal standard is not meant to be limiting in any way. Any appropriate chemical species, easily determined by one in the art, may be used as an internal standard for vitamin B2 quantitation.

EXAMPLES

Example 1

Reagent and Sample Preparation

Two internal standard solutions were prepared with $^{13}C$, $^{15}N_2$-vitamin B2 (Moravek Biomedicals, Inc., custom made, or equivalent). A $^{13}C$, $^{15}N_2$-vitamin B2 internal standard stock solution of 300 μmol/L $^{13}C$, $^{15}N_2$-vitamin B2 in water was prepared. A 500 μL portion of this solution was then diluted to 1 L with water to prepare a $^{13}C$, $^{15}N_2$-vitamin B2 internal standard working solution of 150 nmol/L.

Three calibrant solutions were prepared with vitamin B2 (U.S. Pharmacopia, Cat. No. 1603006, or equivalent). First, a vitamin B2 calibrant stock solution of about 300 μmol/L vitamin B2 in water was prepared. 10 mL of this solution was then diluted with about 90 mL water to prepare a vitamin B2 intermediate calibrant solution of about 30 μmol/L. 2.5 mL of the intermediate calibrant solution was then added to 497.5 mL of blank human serum (Biocell Laboratories, Inc., Cat. No. 1131-00, or equivalent) to prepare a vitamin B2 calibrant working solution of 150 nmol/L.

Portions of the 150 nmol/L vitamin B2 calibrant working solution were then diluted with blank serum to prepare aliquots at 120 nmol/L, 75 nmol/L, 60 nmol/L, 30 nmol/L, 15 nmol/L, and 7.5 nmol/L vitamin B2.

Plasma samples were prepared by collecting blood specimens in EDTA Vacutainer tubes and protected from light. The collected specimens were then frozen for storage and/or transport.

In preparation for analysis, frozen specimens were allowed to thaw and centrifuged at 4000 rpm and 5° C. for 10 minutes. A 200 μL aliquot of the top layer of each centrifuged specimen was then transferred to a well in a 96 well sample tray. 200 μL aliquots of a blank and calibrants at 150 nmol/L, 120 nmol/L, 75 nmol/L, 60 nmol/L 30 nmol/L, 15 nmol/L, and 7.5 nmol/L were also transferred to wells in the sample tray. 800 μL of the 150 nmol/L internal standard working solution was then added to each sample, blank, and calibrant in the tray.

Example 2

Extraction of Vitamin B2 from Samples using Liquid Chromatography

Sample injection was performed with a Cohesive Technologies Aria TLX-4 TFLC system using Aria OS V 1.5.1 or newer software. This system allows for simultaneous chromatography of up to four samples. In the Examples described below, up to three channels were used for simultaneous chromatography of three samples.

For each channel, the TFLC system automatically injected 60 μL of the above prepared samples into a Cyclone MCX column (60 μm particle size, 1.0×50 mm, from Cohesive Technologies, Inc.) packed with large particles. The samples were loaded at a high flow rate (2.0 mL/min, loading reagent 100% water) to create turbulence inside the extraction column. This turbulence ensured optimized binding of vitamin B2 to the large particles in the column and the passage of residual protein and debris to waste.

Following loading, the sample was eluted off to the analytical column (polar embedded C-18 Atlantis T3 analytical column from Waters Corp. (5 μm particle size, 50×4.6 mm), or equivalent) with an eluting solvent of 20% acetonitrile, 79.4% water, 0.5% ammonium formate. and 0.1% formic acid. The HPLC gradient was applied to the analytical column, to separate vitamin B2 from other analytes contained in the sample. Mobile phase A was 0.1% formic acid in water and mobile phase B was 0.1% formic acid in acetonitrile. The HPLC gradient started with a 30% organic gradient which was ramped to 50% in approximately 30 seconds, then ramped to 100% in approximately 50 seconds.

The separated samples were then subjected to MS/MS for quantitation of vitamin B2.

Example 3

Detection and Quantitation of Vitamin B2 by MS/MS

MS/MS was performed using a Finnigan TSQ Quantum Ultra MS/MS system (Thermo Electron Corporation) The following software programs, all from Thermo Electron, were used in the Examples described herein: Quantum Tune Master V 1.2 or newer, Xcalibur V 1.4 SR1 or newer, TSQ Quantum 1.4 or newer, and LCQuan V 2.0 with SP1 or newer. Liquid solvent/analyte exiting the analytical column flowed to the heated nebulizer interface of the MS/MS analyzer. The solvent/analyte mixture was converted to vapor in the heated tubing of the interface. Analytes in the nebulized solvent were ionized by ESI.

Ions passed to the first quadrupole (Q1), which selected ions with a mass to charge ratio of 377.2±0.50 m/z. Tons entering quadrupole 2 (Q2) collided with argon gas to generate ion fragments, which were passed to quadrupole 3 (Q3) for further selection. Simultaneously, the same process using isotope dilution mass spectrometry was carried out with an internal standard, $^{13}C$, $^{15}N_2$-vitamin B2. The following mass transitions were used for detection and quantitation during validation on positive polarity.

TABLE 1

Mass Transitions for vitamin B2 and $^{13}$C, $^{15}$N$_2$-vitamin B2 (Positive Polarity)

| Analyte | Precursor Ion (m/z) | Product Ion (m/z) |
|---|---|---|
| vitamin B2 | 377.2 | 243.2 |
| $^{13}$C, $^{15}$N$_2$-vitamin B2 | 380.2 | 246.2 |

Figure 1B:
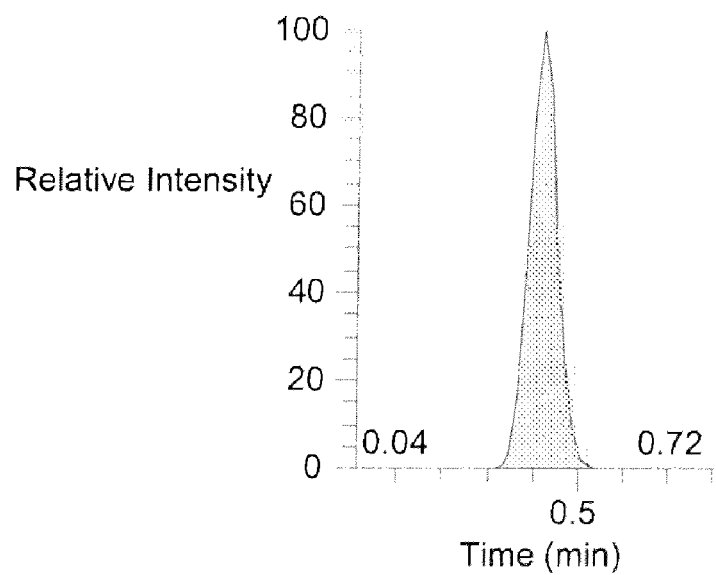

Exemplary chromatograms for vitamin B2 and $^{13}$C, $^{15}$N$_2$-vitamin B2 (internal standard) are found in FIGS. 1A-B.

Example 4

Intra-Assay and Inter-Assay Precision and Accuracy

Four quality control (QC) pools covering the reportable range of the assay were prepared from blank human serum (Biocell Laboratories, Inc., Cat. No. 1131-00) spiked with vitamin B2 to a concentration of 12.5, 25, 50, and 100 nmol/L.

Ten aliquots from each of the four QC pools were analyzed in a single assay to determine the coefficient of variation (CV (%)) of a sample within an assay. Results are found in Table 2. All accuracies are within an acceptable range of 85 % to 115%.

TABLE 2

Intra-Assay Variation and Accuracy for vitamin B2

| Sample | Level I (12.5 nmol/L) | Level II (25 nmol/L) | Level III (50 nmol/L) | Level IV (100 nmol/L) |
|---|---|---|---|---|
| 1 | 12.1 | 26.8 | 49.0 | 97.0 |
| 2 | 14.2 | 26.2 | 51.0 | 101.7 |
| 3 | 11.0 | 27.4 | 45.5 | 96.9 |
| 4 | 14.7 | 22.9 | 46.5 | 96.7 |
| 5 | 10.0 | 27.1 | 48.0 | 94.7 |
| 6 | 14.0 | 26.8 | 48.6 | 92.0 |
| 7 | 12.9 | 23.3 | 48.3 | 97.8 |
| 8 | 12.0 | 24.6 | 47.6 | 96.8 |
| 9 | 12.7 | 26.0 | 47.7 | 98.1 |
| 10 | 13.6 | 27.4 | 50.7 | 93.1 |
| Mean (nmol/dL) | 12.7 | 25.9 | 48.3 | 96.5 |
| Standard Deviation (nmol/dL) | 1.5 | 1.7 | 1.7 | 2.7 |
| CV (%) | 11.7% | 6.5% | 3.5% | 2.8% |
| Accuracy (%) | 101.7% | 103.4% | 96.6% | 96.5% |

Ten aliquots of each of the same four QC pools were assayed over five days to determine the coefficient of variation (CV (%)) between assays. Results are found in Table 3, All accuracies are within an acceptable range of 85% to 115%.

TABLE 3

Inter-Assay Variation and Accuracy

| Day | Mean Measured Value | | | |
|---|---|---|---|---|
| | Level I (12.5 nmol/L) | Level II (25 nmol/L) | Level III (50 nmol/L) | Level IV (100 nmol/L) |
| 1 | 12.6 | 20.2 | 50.0 | 102.5 |
| 2 | 11.9 | 23.5 | 48.4 | 96.8 |
| 3 | 13.6 | 27.1 | 55.2 | 102.9 |
| 4 | 12.1 | 27.4 | 45.5 | 96.9 |
| 5 | 11.0 | 23.0 | 51.9 | 92.8 |

TABLE 3-continued

Inter-Assay Variation and Accuracy

| Day | Mean Measured Value | | | |
|---|---|---|---|---|
| | Level I (12.5 nmol/L) | Level II (25 nmol/L) | Level III (50 nmol/L) | Level IV (100 nmol/L) |
| Mean (nmol/dL) | 12.4 | 25.0 | 49.2 | 98.9 |
| Standard Deviation (nmol/dL) | 1.1 | 2.1 | 3.2 | 6.4 |
| CV (%) | 8.6 | 8.6 | 6.5 | 6.5 |
| Accuracy (%) | 99.5 | 99.9 | 98.4 | 98.9 |

Example 5

Analytical Sensitivity: Lower Limit of Quantitation (LLOQ) and Limit of Detection (LOD)

Figure 2:
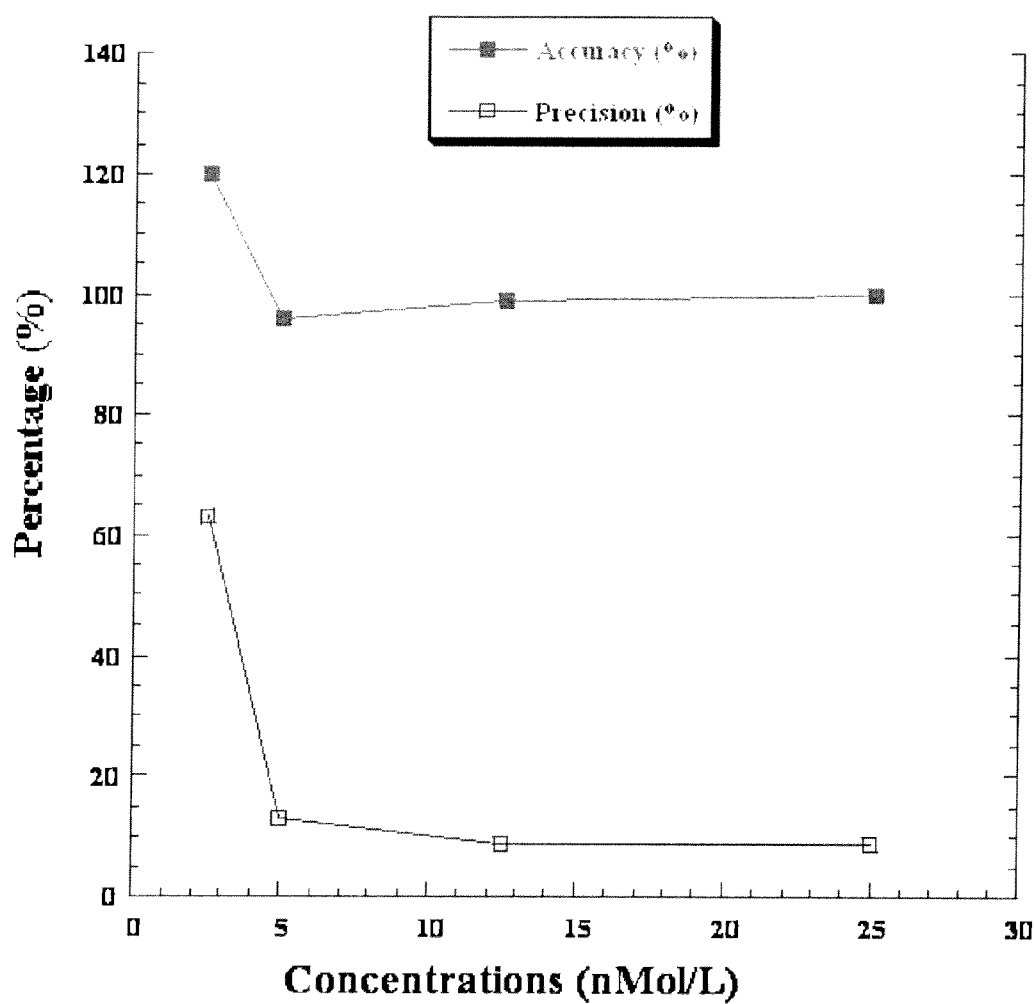
FIG. 2 shows a plot of the coefficient of variation and accuracy of assays of four standards used to determine the lower limit of quantitation of the vitamin B2 assay. Details are discussed in Example 5.

The LLOQ is the point where measurements become quantitatively meaningful. The analyte response at this LLOQ is identifiable discrete and reproducible with a precision of greater than 20%. The LLOQ was determined by assaying ten duplicates of blank human serum samples spiked with vitamin B2 to concentrations of 2.5, 5, 12.5, and 25 nmol/L, then determining the reproducibility. Analysis of the collected data indicates that samples with concentrations of about 5 nmol/mL or above had CVs less than 20%, while samples with concentrations lower than 5 nmol/L had CVs greater than 20%. Thus. the LLOQ of this assay was determined to be 5 nmol/L. The collected data is shown plotted in FIG. 2.

The LOD is the point at which a value is beyond the uncertainty associated with its measurement and is defined as three standard deviations from the zero concentration. To determine the LOD for the vitamin B2 assay, six replicates of blank human serum were assayed, and the results analyzed. The LOD for this assay of 2.7 nmol/L.

Example 6

Vitamin B2 Reportable Range and Linearity

Figure 3:
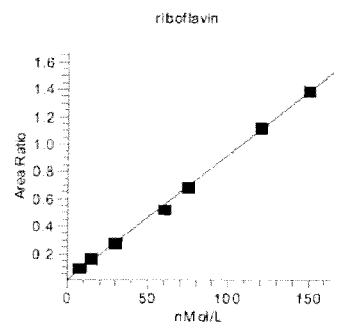
FIG. 3 shows plots of the linearity of quantitation of vitamin B2 in serially diluted stock samples for three channels of a four channel TFLC-MS/MS system conducted over two days. Details are described in Example 6.
Figure 3:
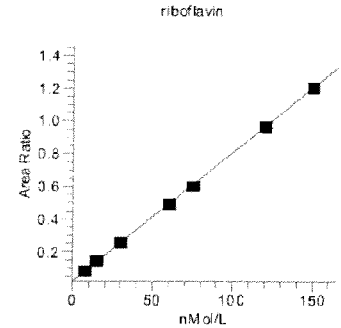
Figure 3:
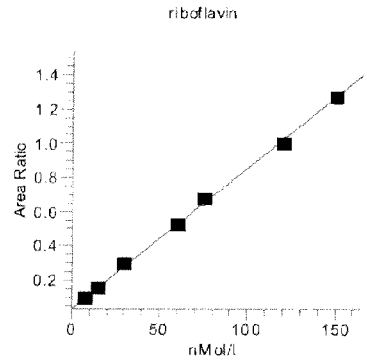
Figure 3:
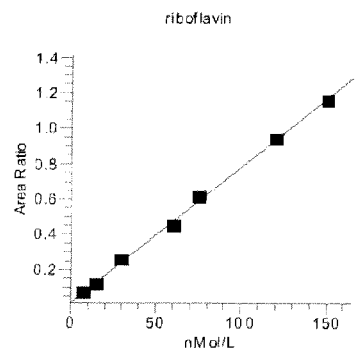
Figure 3:
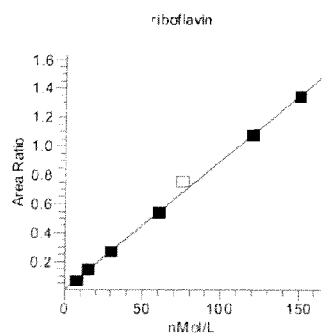
Figure 3:
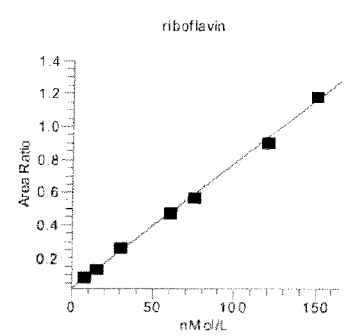

To establish the linearity of vitamin B detection in the assay, on two different days three separate assays were conducted utilizing three channels of the multiplexed TFLC system. Each assay included seven spiked blank serum standards at concentrations ranging from 7.5 nmol/L to 150.0 nmol/L. Linear regressions were calculated for each assay, yielding correlation coefficients of 0.9981 or greater (see Table 4, below). Graphs showing the linearty of the data are shown in FIG. 3.

TABLE 4

Fitting parameters for linearity studies

| Assay | Fitting Parameters | Goodness of Fit ($R^2$) |
|---|---|---|
| Column 1 (Day 1) | Y = 0.00745235 + 0.00916646 * X | 0.9987 |
| Column 2 (Day 1) | Y = 0.0310187 + 0.00827027 * X | 0.9981 |
| Column 3 (Day 1) | Y = 0.00721216 + 0.0089436 * X | 0.9999 |
| Column 1 (Day 2) | Y = 0.0182602 + 0.00791278 * X | 0.9995 |
| Column 2 (Day 2) | Y = 0.0104523 + 0.00771775 * X | 0.9988 |
| Column 3 (Day 2) | Y = 0.0170813 + 0.00763554 * X | 0.9981 |

Example 7

Matrix Specificity

Figure 4A:
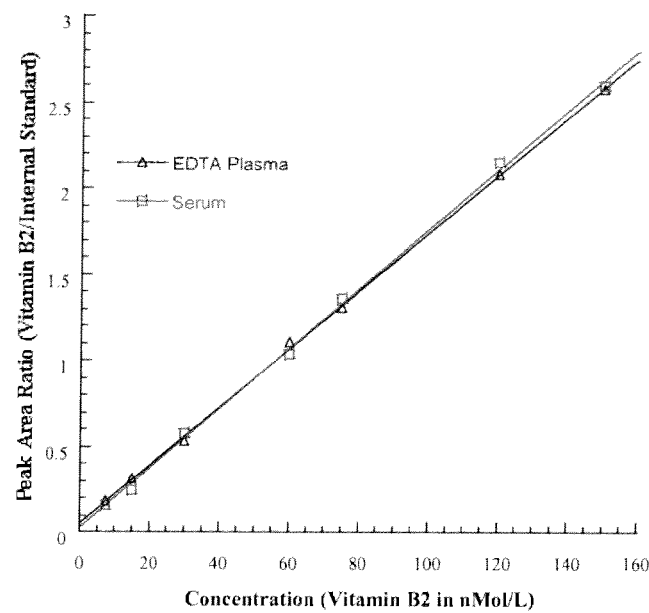
FIGS. 4A-C show the correlation of determination of vitamin B2 in serum and vitamin B2 in EDTA plasma by TFLC-MS/MS determination. Details are described in Example 7.
Figure 4B:
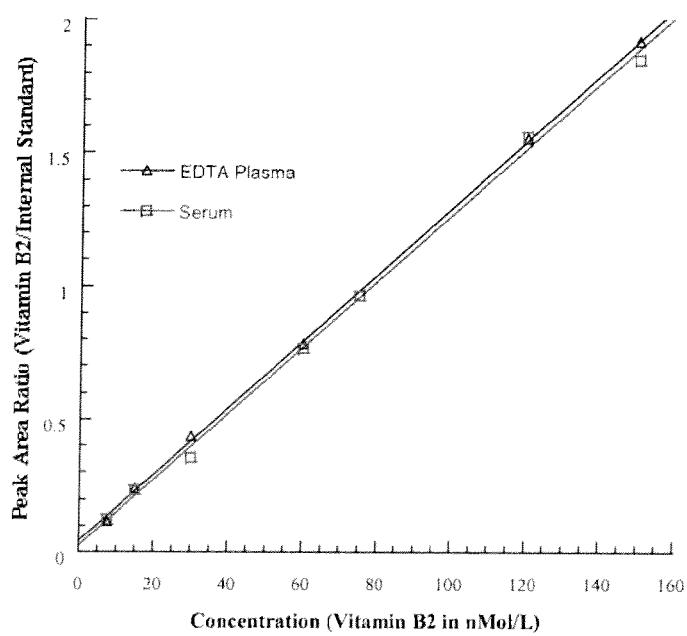
Figure 4C:
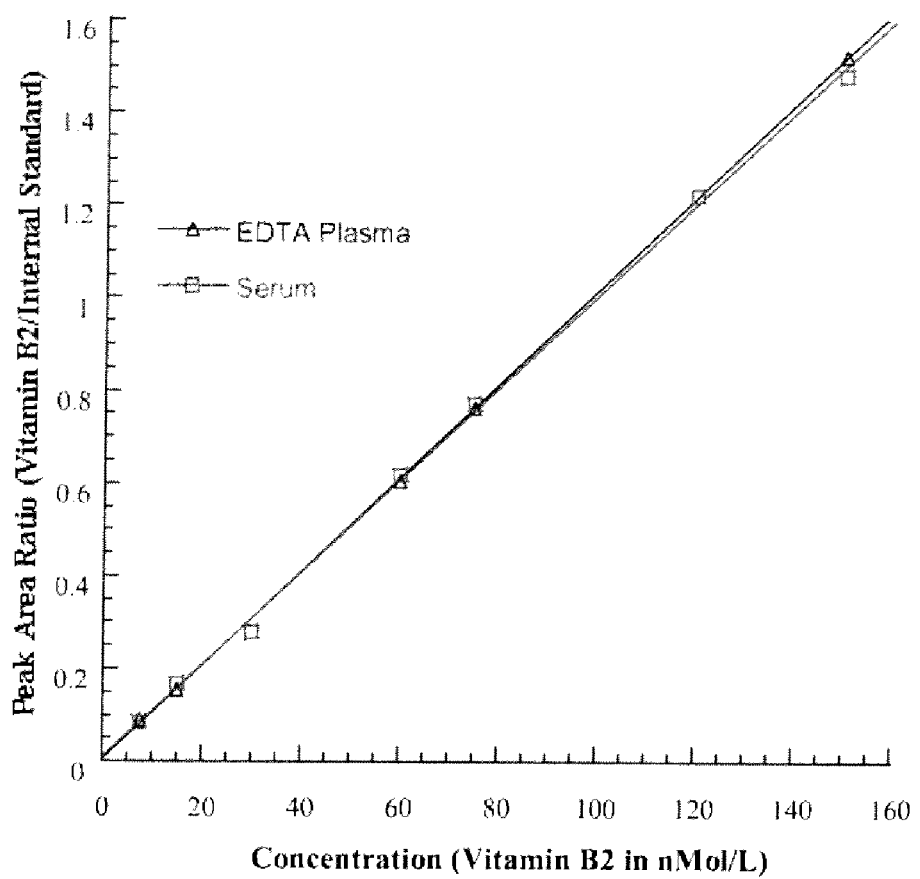

Matrix specificity was evaluated using human stripped serum and in-house prepared blank EDTA plasma specimens. Samples of both matrices spiked to seven concentration levels ranging from 7.5 nmol/L to 150.0 nmol/L were analyzed over three days and the results compared. The study indicated that both matrices could be used for the assay. The results of these studies are presented in FIGS. 4A-C.

Example 8

Interference Studies

Eighteen drugs or compounds were investigated on their possible interference on vitamin B2 in this assay. These drugs are acetyl salicylic acid, 4-acetamidophenol, amiodarone, N-desethyl amidorone, felbamate, hydroxyzine hydrochloride, mycophenolic acid, fiunitrazepam, fluoxetine, tacrolimus, rapamycin, cyclosporine, flecainide, propafenone, clozapine, norclozapine, lidocaine, and sirolimus. These drugs were mixed and spiked at a concentration of 50 ng/mL each to plasma samples containing vitamin B2 at three concentration levels (25 nmol/L, 50 nmol/L, and 100 nmol/L). The samples were assayed together with vitamin B2 plasma samples with no drug additives, and results were compared. The percentage yielded from the drug additive versus the non-additive samples were 90%. 88%. and 92% for the three concentration levels, respectively.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims In addition, where features or aspects of the methods are described in terms of Markush groups, those skilled in the art will recognize that the invention is also thereby described in terms of any individual member or subgroup of members of the Markush group.

That which is claimed is:

1. A method for determining the amount of vitamin B2 in a biological sample when taken from a patient, said method comprising:
   a. subjecting the sample, purified by mixed-mode turbulent flow liquid chromatography (TFLC) and high performance liquid chromatography (HPLC), to ionization under conditions suitable to produce one or more ions detectable by mass spectrometry;
   b. determining the amount of said one or more ions by tandem mass spectrometry; and
   c. using the amount of said one or more ions to determine the amount of vitamin B2 in the sample.

2. A method for determining the amount of vitamin B2 in a sample when taken from a patient, said method comprising:
   a. purifying a biological sample, comprising:
      i. subjecting the sample to a mixed-mode turbulent flow liquid chromatography (TFLC) column under conditions whereby vitamin B2 is retained by the mixed-mode TFLC column;
      ii. washing the mixed-mode TFLC column with a first mobile phase under conditions whereby non-retained materials from the sample are washed from the mixed-mode TFLC;
      iii. applying a second mobile phase to the mixed-mode TFLC column, whereby retained vitamin B2 is eluted from the mixed-mode TFLC column; and
      iv. applying vitamin B2 eluted from the mixed-mode TFLC column to a high performance liquid chromatography column;
   b. subjecting vitamin B2 from said sample to an ionization source under conditions suitable to produce one or more ions detectable by mass spectrometry;
   c. determining the amount of said one or more ions by tandem mass spectrometry; and
   d. using the amount of said one or more ions to determine the amount of vitamin B2 in the sample.

* * * * *